US012669432B2

(12) United States Patent
Sun et al.

(10) Patent No.: US 12,669,432 B2
(45) Date of Patent: Jun. 30, 2026

(54) METHOD FOR DETECTING AN OBJECT CONTAINING RECYCLED PLASTIC MATERIALS BY QUALITATIVE AND SEMI-QUANTITATIVE DETECTIONS

(71) Applicant: SGS TAIWAN LIMITED, New Taipei City (TW)

(72) Inventors: Hsiu-Feng Sun, New Taipei City (TW); Chun-Wei Chen, New Taipei City (TW); Li-Hsiang Lin, New Taipei City (TW); Chang-Ting Tsai, New Taipei City (TW)

(73) Assignee: SGS TAIWAN LIMITED, New Taipei City (TW)

( * ) Notice: Subject to any disclaimer, the term of this patent is extended or adjusted under 35 U.S.C. 154(b) by 108 days.

(21) Appl. No.: 18/910,807

(22) Filed: Oct. 9, 2024

(65) Prior Publication Data

US 2025/0123200 A1     Apr. 17, 2025

(30) Foreign Application Priority Data

Oct. 13, 2023     (TW) ................................. 112139250

(51) Int. Cl.
  *G01N 21/33*       (2006.01)
  *G01N 21/64*       (2006.01)
  *G01N 33/44*       (2006.01)
(52) U.S. Cl.
  CPC ............. *G01N 21/33* (2013.01); *G01N 21/64* (2013.01); *G01N 33/442* (2013.01)

(58) Field of Classification Search
  CPC ....... G01N 21/33; G01N 21/64; G01N 33/442
  See application file for complete search history.

(56) References Cited

FOREIGN PATENT DOCUMENTS

| | | | | |
|---|---|---|---|---|
| CN | 108918450 A | 11/2018 | | |
| CN | 115096751 A | 9/2022 | | |
| CN | 115356230 A | 11/2022 | | |
| JP | 2017015503 A | 1/2017 | | |
| TW | 202301192 A | * 1/2023 | ............. | B29B 17/02 |

* cited by examiner

*Primary Examiner* — Jamil Ahmed
(74) *Attorney, Agent, or Firm* — WPAT, PC

(57)                ABSTRACT

A method for detecting an object containing recycled plastic materials by qualitative and semi-quantitative detections is revealed, in which observing a yellowing condition of the object using a first light source, and illuminating the object using a second light source for observing a defect amount on the surface image of the object. When a yellowing index of the object is smaller than a standard yellowing index as well as a second defect condition is greater than a first defect condition, and an activation energy value of the object from a thermogravimetric analyzer is smaller than a standard activation energy value, the object does contain recycled plastic materials. Since the spectrums of recycled PET and native PET are different, the object contains recycled PET and the proportion of the recycled PET are determined according to the spectrums of fluorescent spectrum analysis and the difference ratio between the spectrums respectively.

22 Claims, 13 Drawing Sheets

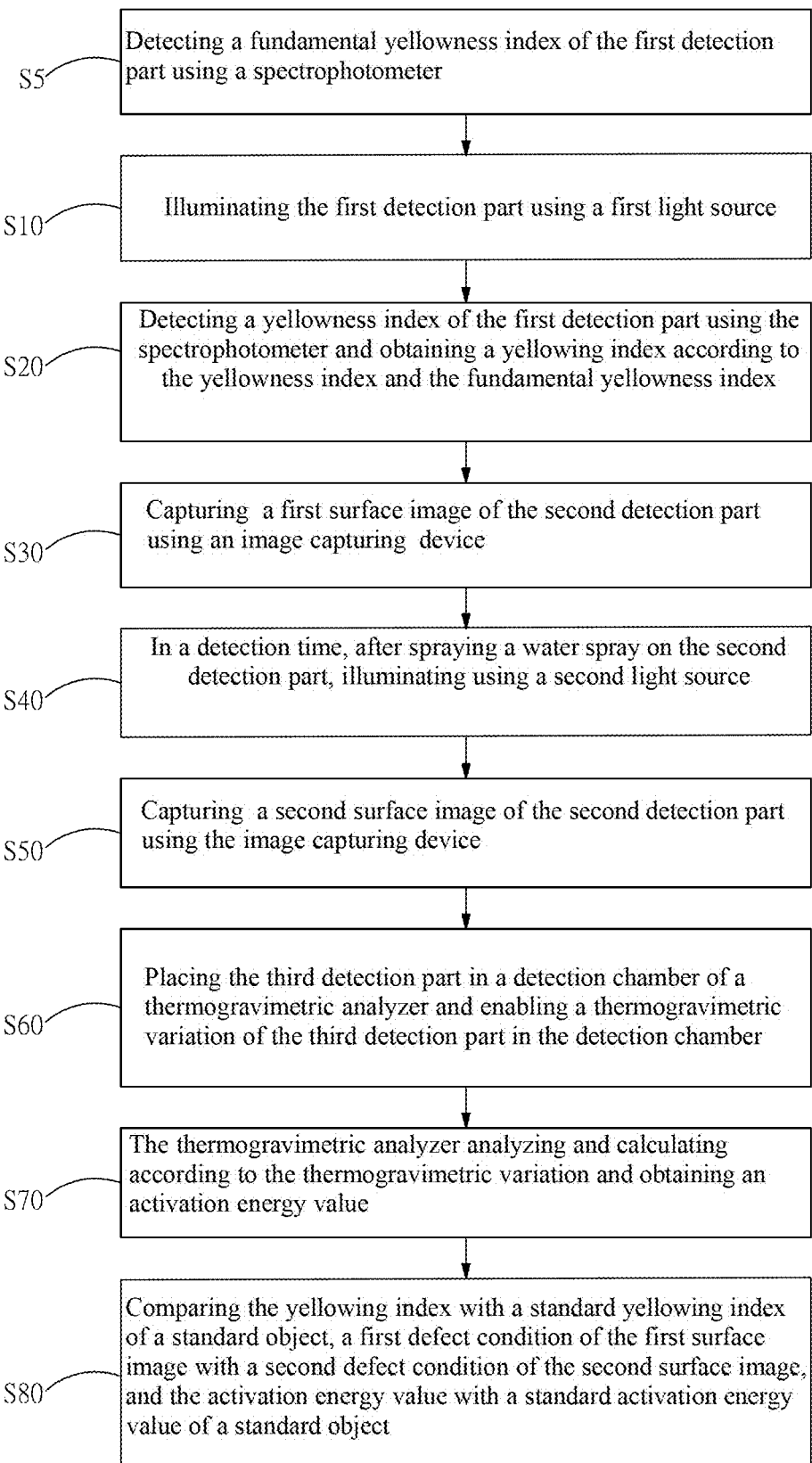

S5 — Detecting a fundamental yellowness index of the first detection part using a spectrophotometer S10 — Illuminating the first detection part using a first light source S20 — Detecting a yellowness index of the first detection part using the spectrophotometer and obtaining a yellowing index according to the yellowness index and the fundamental yellowness index S30 — Capturing a first surface image of the second detection part using an image capturing device S40 — In a detection time, after spraying a water spray on the second detection part, illuminating using a second light source S50 — Capturing a second surface image of the second detection part using the image capturing device S60 — Placing the third detection part in a detection chamber of a thermogravimetric analyzer and enabling a thermogravimetric variation of the third detection part in the detection chamber S70 — The thermogravimetric analyzer analyzing and calculating according to the thermogravimetric variation and obtaining an activation energy value S80 — Comparing the yellowing index with a standard yellowing index of a standard object, a first defect condition of the first surface image with a second defect condition of the second surface image, and the activation energy value with a standard activation energy value of a standard object

Fig. 1B

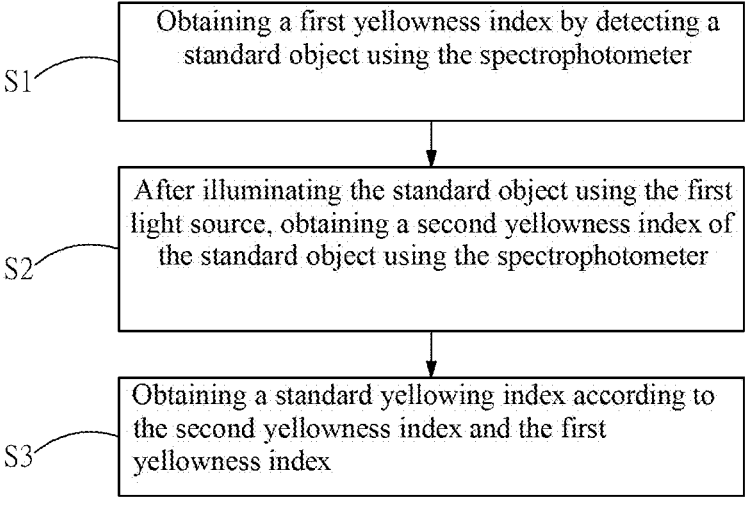

S1 — Obtaining a first yellowness index by detecting a standard object using the spectrophotometer S2 — After illuminating the standard object using the first light source, obtaining a second yellowness index of the standard object using the spectrophotometer S3 — Obtaining a standard yellowing index according to the second yellowness index and the first yellowness index

Fig. 1D

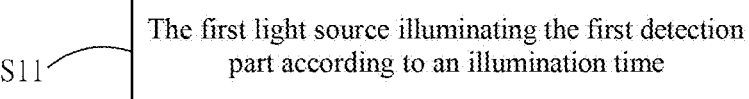

S11 — The first light source illuminating the first detection part according to an illumination time

Fig. 1E

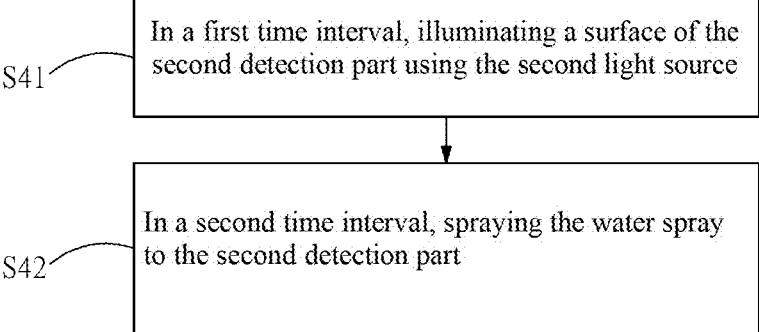

S41 — In a first time interval, illuminating a surface of the second detection part using the second light source S42 — In a second time interval, spraying the water spray to the second detection part

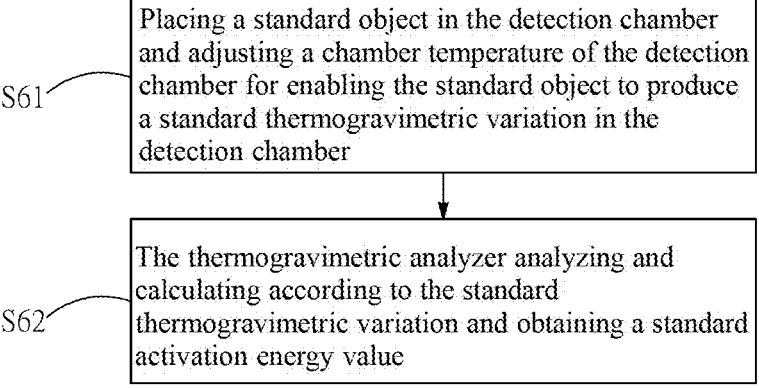

Placing a standard object in the detection chamber and adjusting a chamber temperature of the detection chamber for enabling the standard object to produce a standard thermogravimetric variation in the detection chamber

S62

The thermogravimetric analyzer analyzing and calculating according to the standard thermogravimetric variation and obtaining a standard activation energy value

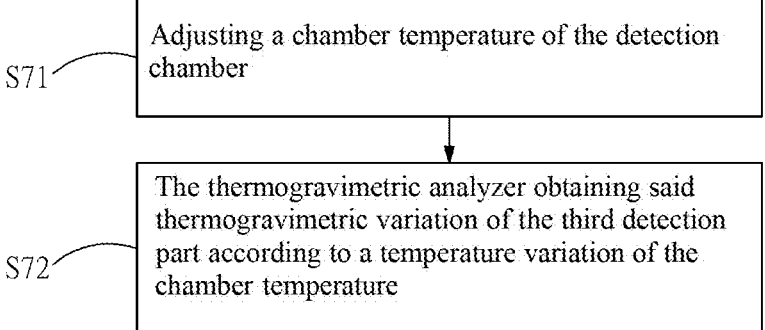

Adjusting a chamber temperature of the detection chamber

S72

The thermogravimetric analyzer obtaining said thermogravimetric variation of the third detection part according to a temperature variation of the chamber temperature

Fig. 1H

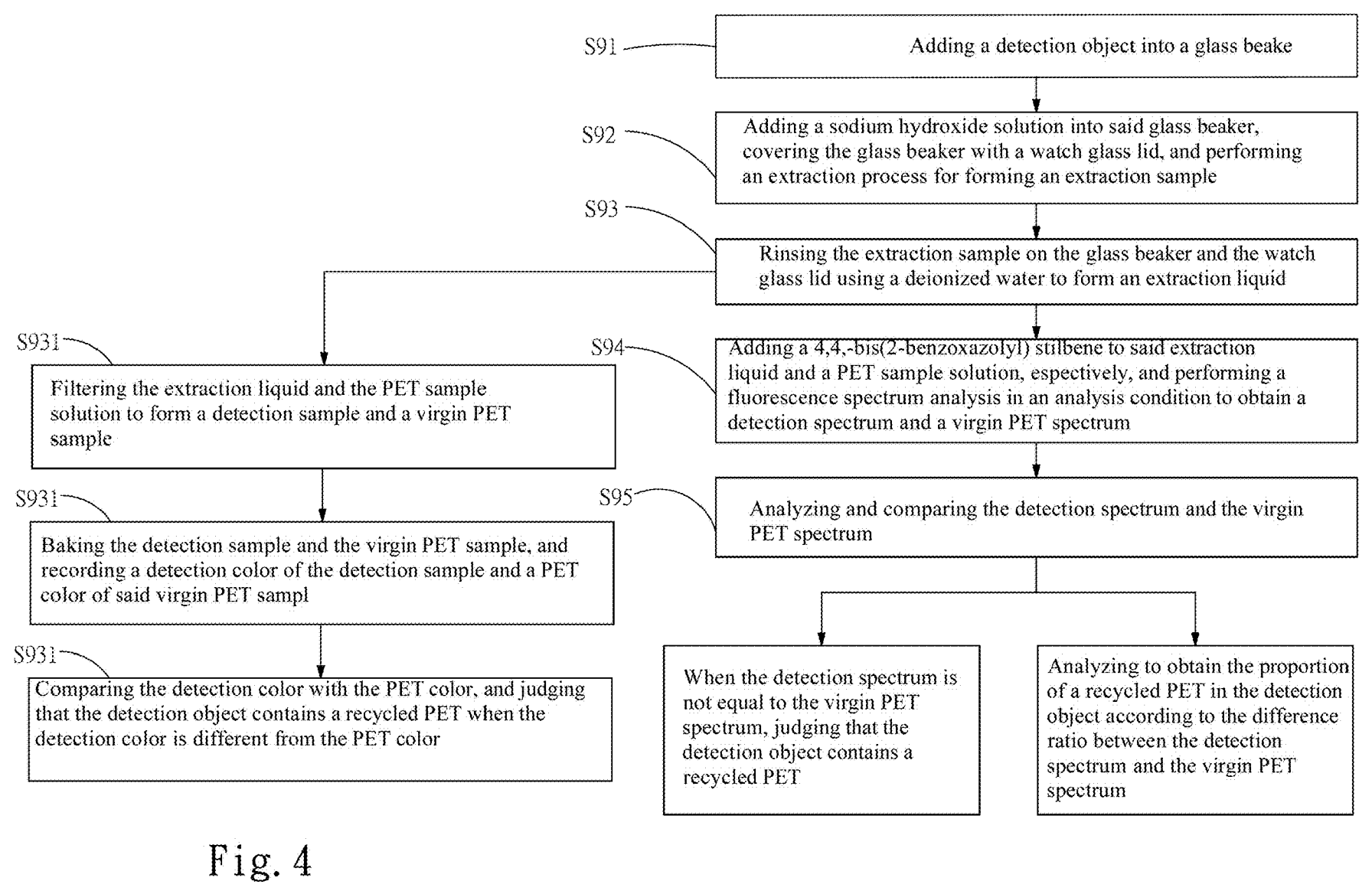

S91 — Adding a detection object into a glass beake

S92 — Adding a sodium hydroxide solution into said glass beaker, covering the glass beaker with a watch glass lid, and performing an extraction process for forming an extraction sample S93 — Rinsing the extraction sample on the glass beaker and the watch glass lid using a deionized water to form an extraction liquid S94 — Adding a 4,4,-bis(2-benzoxazolyl) stilbene to said extraction liquid and a PET sample solution, respectively, and performing a fluorescence spectrum analysis in an analysis condition to obtain a detection spectrum and a virgin PET spectrum S95 — Analyzing and comparing the detection spectrum and the virgin PET spectrum Analyzing to obtain the proportion of a recycled PET in the detection object according to the difference ratio between the detection spectrum and the virgin PET spectrum When the detection spectrum is not equal to the virgin PET spectrum, judging that the detection object contains a recycled PET S931 — Filtering the extraction liquid and the PET sample solution to form a detection sample and a virgin PET sample S931 — Baking the detection sample and the virgin PET sample, and recording a detection color of the detection sample and a PET color of said virgin PET sampl S931 — Comparing the detection color with the PET color, and judging that the detection object contains a recycled PET when the detection color is different from the PET color

Fig. 4

METHOD FOR DETECTING AN OBJECT CONTAINING RECYCLED PLASTIC MATERIALS BY QUALITATIVE AND SEMI-QUANTITATIVE DETECTIONS

FIELD OF THE INVENTION

The present application relates to a method, particularly a method for detecting an object containing recycled plastic materials by qualitative and semi-quantitative detections.

BACKGROUND OF THE INVENTION

With the continuous development of chemistry and chemical engineering technologies, chemical products are more and more widely used in people's lives. As a commonly used chemical product, plastic has become an indispensable thing in people's daily lives. The development of plastic technology has made its varieties be more and more abundant, its properties be diverse, and its functional characteristics be constantly improved.

However, due to the gradual rise of the global trend of environmental protection and pollution prevention, many national governments have begun to require government and commercial institutions to use recycled plastic products (namely, recycled materials). In addition, most companies with major international brands have also designated the goal of using recycled materials. These implements have promoted the development of plastic recycling technology.

The above-mentioned recycled plastics include recycled materials, recycled modified materials, and waste plastics. Recycled materials are not necessarily waste plastics. The main differences between recycled materials and waste plastics are: (1) whether they are reprocessed such as melting and granulating in the factory production line; (2) whether their main plastic components are single or composite components. Waste plastics only require simple cleaning and cutting work, and the ingredients are relatively complex, often containing a variety of plastics. Here, the recycled materials refer to recycled plastic materials that are formed after appropriate treatment and processing. Such recycled materials usually come from the recycling and regeneration of plastic products, such as waste plastic containers, packaging materials, and plastic products.

However, different recycled materials cause some safety concerns. This is because different recycled materials may come from different recycling sources, such as different types of waste plastic products and different recycling processes. Furthermore, there may also be pollutants in the recycled materials, and these pollutants may come from the components of waste plastic products.

Moreover, there is another uncertain factor in recycled materials. Because these recycled materials are usually not stored properly and can often be seen outdoors, leaving them exposed to wind, sun, and rain. This makes recycled materials more prone to brittleness.

The more recycled materials are added to a product while the more serious the plastic degradation will be, thereby, further reducing the original structural strength of the plastic, which will cause problem of fragile and fracture, especially where places of the plastic that must receive stress.

Accordingly, before using recycled materials, it is necessary to carefully consider whether the quality and performance of the recycled materials can meet the requirements of specific applications and conduct corresponding tests and verification. Furthermore, appropriate analysis and inspection of products adopting recycled materials need to be carried out to ensure that the use of recycled materials complies with relevant regulations and standards.

Nowadays, various manufacturers currently use third-party notary organizations to confirm whether recycled materials are contained in products through audit methods, and confirm the proportion of recycled materials in products. This method may only certify the proportion of recycled materials added to the current product in the current batch.

Unfortunately, the above-mentioned auditing and certification method still cannot guarantee that the manufacturer adds recycled materials in each batch according to the declaration of recycled material proportion, so consumers or users have no way of knowing whether recycled materials are actually contained in the products, knowing what kind of recycled materials are contained in products, and knowing the related proportion of recycled materials added to current products. Thereby, to provide an accurate verification of the content of recycled materials in plastics will be a challenge.

Accordingly, how to provide a quick way to determine whether recycled materials are added to a product and further confirm the approximate proportion of recycled materials added to the product has become a problem to be solved by personnels skilled in the art.

SUMMARY OF THE INVENTION

An objective of the present application is to provide a method for detecting an object containing recycled plastic materials. The method observes the yellowing condition of an object using a first light source. By illuminating the object using a second light source, an image extraction device observes the defect condition through the image of object surface. Then a thermogravimetric analyzer is used to analyze and calculate the activation energy value of the object according to the thermogravimetric variation of the object. According to the yellowing condition, the surface image, and the activation energy value, whether the object contains recycled plastic materials can be judged. According to the method of the present application, whether an object contains recycled plastic materials can be judged quickly.

To achieve the above objective, the present application provides a method for detecting an object containing recycled plastic materials. The method detects a first detection part, a second detection part, and a third detection part of an object and comprises steps of: detecting a fundamental yellowness index of the first detection part using a spectrophotometer; illuminating the first detection part using a first light source; detecting a yellowness index of the first detection part using the spectrophotometer and obtaining a yellowing index according to the yellowness index and the fundamental yellowness index; capturing a first surface image of the second detection part using an image extraction device; in a detection time of detecting the second detection part, after spraying a water spray on the second detection part, illuminating the second detection part using a second light source; capturing a second surface image of the second detection part using the image extraction device; placing the third detection part in a detection chamber of a thermogravimetric analyzer and enabling a thermogravimetric variation of the third detection part in the detection chamber; the thermogravimetric analyzer analyzing and calculating according to the thermogravimetric variation and obtaining an activation energy value; comparing the yellowing index with a standard yellowing index of a standard object, a first defect condition of the first surface image with a second defect condition of the second surface image, and the activation energy value with a standard activation energy value of a standard object; where when the yellowing index is smaller than the standard yellowing index, the second defect condition is greater than the first defect condition, and the activation energy value is smaller than the standard activation energy value, the object is judged to contain recycled plastic materials.

According to an embodiment of the present application, in the step of illuminating the first detection part using a first light source, the first light source includes a UV light source, a xenon arc light source, a carbon arc light source, or a mercury light source.

According to an embodiment of the present application, the wavelength of the UV light source is from 200 nm to 400 nm.

According to an embodiment of the present application, before the step of detecting a fundamental yellowness index of the first detection part using a spectrophotometer, the method further comprises steps of: obtaining a first yellowness index by detecting a standard object using the spectrophotometer; after illuminating the standard object using the first light source, obtaining a second yellowness index of the standard object using the spectrophotometer; obtaining a standard yellowing index according to the second yellowness index and the first yellowness index; where the standard object is an object containing no recycled plastic material.

According to an embodiment of the present application, in the step of illuminating the first detection part using a first light source, the method further comprises a step of the first light source illuminating the first detection part according to an illumination time; where the illumination time from 24 to 450 hours.

According to an embodiment of the present application, in the step of in the detection time of detecting the second detection part, after spraying a water spray on the second detection part, illuminating the second detection part using a second light source, the second light source includes a UV light source, a xenon arc light source, a carbon arc light source, or a mercury light source.

According to an embodiment of the present application, in the step of in the detection time of detecting the second detection part, after spraying a water spray on the second detection part, illuminating the second detection part using a second light source, the method further comprises steps of: in a first time interval, illuminating a surface of the second detection part using the second light source, where the surface is at a first temperature from 50 to 80° C.; and in a second time interval, spraying the water spray to the second detection part and illuminating the second detection part using the second light source, where the second light source is shut off while spaying the water spray; where the first time interval and the second time interval are executed repeatedly and cyclically in the detection time.

According to an embodiment of the present application, where in the step of in a first time interval, illuminating a surface of the second detection part using the second light source, the first time interval is from 85 to 150 minutes.

According to an embodiment of the present application, where in the step of in a second time interval, spraying the water spray to the second detection part and illuminating the second detection part using the second light source, the second time interval is from 5 to 60 minutes.

According to an embodiment of the present application, before the step of placing the third detection part in a detection chamber of a thermogravimetric analyzer and enabling a thermogravimetric variation of the third detection part in the detection chamber, the method further comprises steps of: placing a standard object in the detection chamber and adjusting a chamber temperature of the detection chamber for enabling the standard object to produce a standard thermogravimetric variation in the detection chamber; and the thermogravimetric analyzer analyzing and calculating according to the thermogravimetric variation and obtaining a standard activation energy value; where the chamber temperature is from 20 to 1000° C.

According to an embodiment of the present application, in the step of the thermogravimetric analyzer analyzing and calculating according to the thermogravimetric variation and obtaining an activation energy value, the method further comprises steps of: adjusting a chamber temperature of the detection chamber, where the chamber temperature is from 20 to 1000° C.; and the thermogravimetric analyzer obtaining the thermogravimetric variation of the third detection part according to a temperature variation of the chamber temperature.

According to an embodiment of the present application, the object is composed of recycled plastic materials and/or non-recycled plastic materials. Furthermore, the recycled plastic materials and the non-recycled plastic materials are selected from the group consisting of polyethylene, polypropylene, polyethylene terephthalate, polycarbonate, copolymer of polycarbonate and acrylonitrile butadiene styrene, polystyrene, or thermoplastic polyurethane.

In addition, in view of the fact that environmental protection regulations in various countries have set a target of 25% for the use of recycled plastics in the blending of recycled materials for non-food grade plastic containers, the detection of the proportion of recycled materials added to plastic containers is an important measurement method.

According to research, the threshold aggregation concentration in fluorescent and nonfluorescent dye-polymer systems depends on the crystallinity of polymer host, the relative solubility of dye (guest), and the number of dye-polymer (guest-host) interactions.

Accordingly, the present application utilizes the difference in bonding and crystallinity between the molecules of plastics with a single component or with a composite component of mixed plastic matrix formed by the reprocessing process of melt granulation using native plastic and added recycled plastic during the plastics manufacturing process. Alkaline solution is used for extraction and detection. The alkaline solution will weaken the bonds of recycled plastics and cause them to become ionized. The difference in bond strength is then used to disperse the fluorophores in the continuous matrix. When the concentration of the fluorescent dye increases and the formation energy and the dissociated recycled plastic molecular groups aggregate, the difference in the intensity of the scattered waves between the native plastics and the recycled plastics can be observed at the double frequency of the excitation light source. Thereby, the method according to the present application can quickly judge whether an object contains recycled plastic materials and determine the proportion of the recycled plastic materials added.

Another objective of the present application is to provide detecting an object containing recycled plastic materials by qualitative and semi-quantitative detections. The spectrum obtained through fluorescence spectrum analysis is used for detecting whether an object contains recycled PET and determining content of recycled PET in the object.

To achieve the above objective, the present application provides a method for detecting an object containing recycled plastic materials, comprising steps of: adding a detection object (undergo a pre-processing procedure in advance, the pre-processing procedure is to cut the detection object into 1 cm×1 cm pieces) into a glass beaker; adding a sodium hydroxide solution into the glass beaker, covering the beaker with a watch glass lid, and performing an extraction process (at the temperature from 105° C. to 125° C. for 70 to 100 minutes) for forming an extraction sample; rinsing the extraction sample on the glass beaker and the watch glass lid using a deionized water to form an extraction liquid; adding a 4,4,-bis(2-benzoxazolyl) stilbene to the extraction liquid and a PET sample solution, respectively, and performing a fluorescence spectrum analysis in an analysis condition (using a fluorescence spectrometer to detect and observe the intensity of the wave at double frequency for polymer bond loss, and observe the signal intensity through the wave signal intensity at double frequency) to obtain a detection spectrum and a native PET spectrum; analyzing and comparing the detection spectrum and the native PET spectrum; and when thev detection spectrum is not equal to the native PET spectrum, judging that the detection object contains a recycled PET (by using the signal intensity at double frequency, it is observed that the signal intensity of the extraction liquid is greater than the signal intensity of the PET sample solution and the signal intensity of the blank solution).

According to an embodiment of the present application, the analysis condition includes that the excitation wavelength is set at 373 nm; the incident slit is set at 5 nm; the emission slit is set at 5 nm; the wavelength scanning range is set from 360 nm to 800 nm; and the scanning rate is set within 120 nm/min.

According to an embodiment of the present application, after the step of rinsing the extraction sample on the glass beaker and the watch glass lid using a deionized water to form an extraction liquid, the method further comprises steps of: filtering the extraction liquid to form a detection sample; baking the detection sample and a native PET sample at a temperature from 90° C. to 120° C. for 6 to 9 hours, and recording a detection color of the detection sample and a PET color of the native PET sample; and comparing the detection color with the PET color, and judging that the detection object contains a recycled PET when the detection color is different from the PET color.

To achieve the above objective, the present application provides a method for detecting an object containing recycled plastic materials by semi-quantitative detections, comprising steps of: adding a detection object (undergo a pre-processing procedure in advance, the pre-processing procedure is to cut the detection object into 1 cm×1 cm pieces) into a glass beaker; adding a sodium hydroxide solution into the glass beaker, covering the glass beaker with a watch glass lid, and performing an extraction process (at the temperature from 105° C. to 125° C. for 70 to 100 minutes) for forming an extraction sample; rinsing the extraction sample on the glass beaker and the watch glass lid using a deionized water to form an extraction liquid; adding 4,4,-bis(2-benzoxazolyl) stilbene to the extraction liquid and a PET sample solution, respectively, and performing fluorescence spectrum analysis in an analysis condition to obtaun a detection spectrum and a native PET spectrum; analyzing and comparing the detection spectrum and the native PET spectrum; and analyzing to give the proportion of a recycled PET in the detection object according to the difference ratio between the detection spectrum and the native PET spectrum.

According to an embodiment of the present application, the analysis condition includes that the excitation wavelength is set at 373 nm; the incident slit is set at 5 nm; the emission slit is set at 5 nm; the wavelength scanning range is set from 360 nm to 800 nm; and the scanning rate is set within 120 nm/min.

BRIEF DESCRIPTION OF DRAWINGS

FIG. 1B shows a flowchart according to an embodiment of the present application;

FIG. 1D shows a flowchart of the standard yellowing index according to an embodiment of the present application;

FIG. 1E shows a flowchart of the first light source according to an embodiment of the present application;

FIG. 1F shows a flowchart of the second light source according to an embodiment of the present application;

FIG. 1G shows a flowchart of the standard activation energy value according to an embodiment of the present application;

FIG. 1H shows a flowchart according to an embodiment of the present application;

FIG. 4 shows a flowchart according to another embodiment of the present application.

DETAILED DESCRIPTION OF THE INVENTION

Figure 1A:
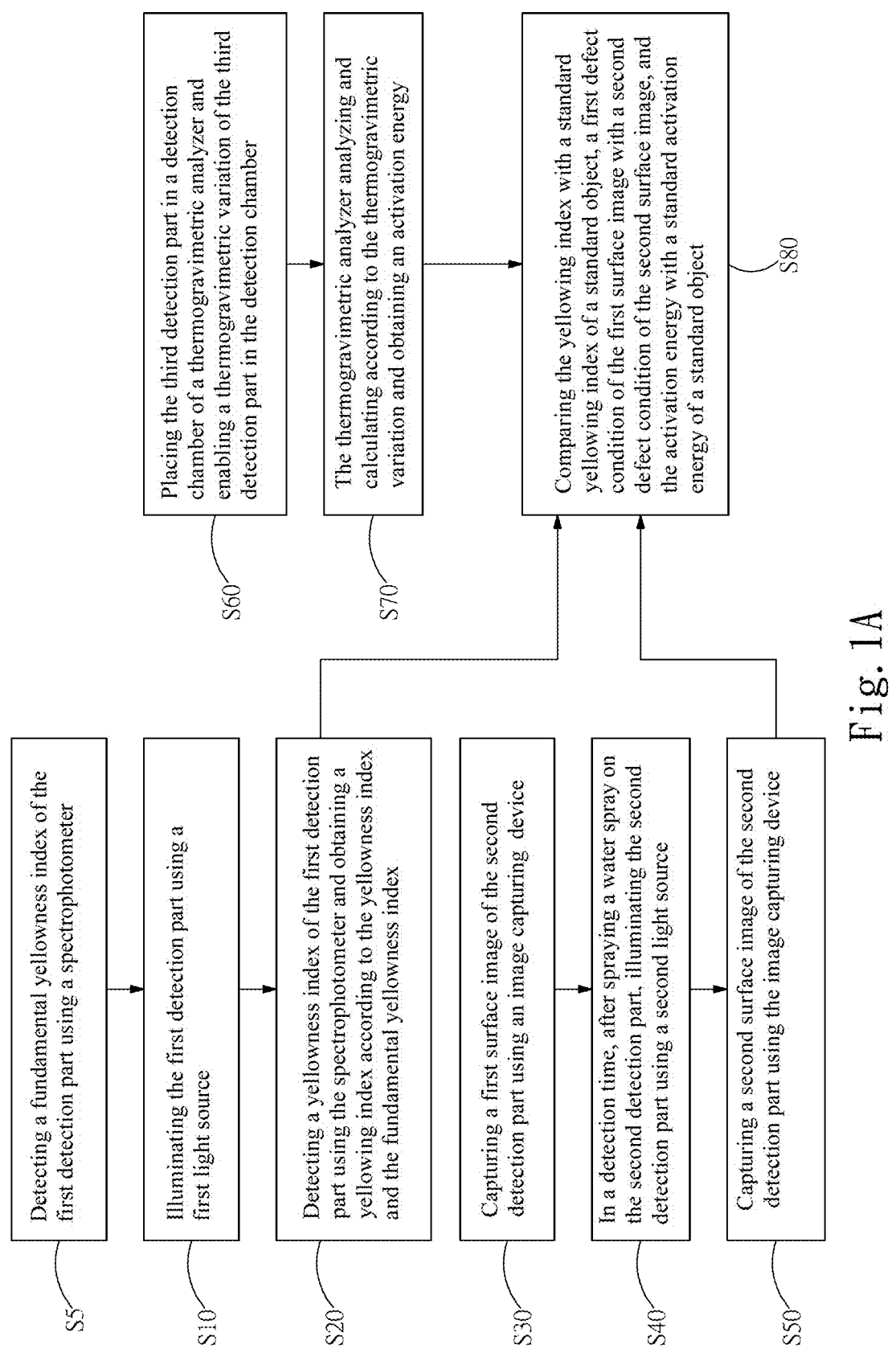
FIG. 1A shows a flowchart according to an embodiment of the present application.

In order to make the structure and characteristics as well as the effectiveness of the present application to be further understood and recognized, the detailed description of the present application is provided as follows along with embodiments and accompanying figures.

It is known that manufacturers rely on third-party notarization units to add recycled plastic materials, and use the total amount of recycled plastic materials to conduct physical audits, as well as using this method to certify the proportion of recycled plastic materials added to products. However, although this method can certify the proportion of recycled plastic materials added to products, there is no guarantee that the manufacturer will add it in each batch according to the declared ratio of recycled plastic materials to non-recycled plastic materials. Therefore, stakeholders have no way of knowing whether products actually contain recycled materials.

The present application uses a first light source, a second light source, and a thermogravimetric analyzer to observe the yellowing condition, the surface image, and the activation energy value of an object. By means of the yellowing condition, the surface image, and the activation energy value of the object, whether recycled plastic materials are added to the objects or products made by manufacturers can be confirmed.

In the following description, various embodiments of the present application are described using figures for describing the present application in detail. Nonetheless, the concepts of the present application can be embodied by various forms. Those embodiments are not used to limit the scope and range of the present application.

First, please refer to FIG. 1B, which shows a flowchart according to an embodiment of the present application. As shown in the figure, the method for detecting an object (which comprising a first detection part, a second detection part, and a third detection part) contains recycled plastic materials according to the present embodiment comprises steps of:

Step S5: Detecting a fundamental yellowness index of the first detection part using a spectrophotometer;

Step S10: Illuminating the first detection part using a first light source;

Step S20: Detecting a yellowness index of the first detection part using the spectrophotometer and obtaining a yellowing index according to the yellowness index and the fundamental yellowness index;

Step S30: Capturing a first surface image of the second detection part using an image extraction device;

Step S40: In a detection time of detecting the second detection part, after spraying a water spray on the second detection part, illuminating the second detection part using a second light source;

Step S50: Capturing a second surface image of the second detection part using the image extraction device;

Step S60: Placing the third detection part in a detection chamber of a thermogravimetric analyzer and enabling a thermogravimetric variation of the third detection part in the detection chamber;

Step S70: The thermogravimetric analyzer analyzing and calculating according to the thermogravimetric variation and obtaining an activation energy value; and Step S80: Comparing the yellowing index with a standard yellowing index of a standard object, a first defect condition of the first surface image with a second defect condition of the second surface image, and the activation energy value with a standard activation energy value of a standard object.

Please refer to FIG. 1A, which shows a flowchart according to an embodiment of the present application. As shown in the figure, in the method for detecting an object containing recycled plastic materials according to the present application, the steps S5, S10, and S20 use the first light source for performing aging test; the steps 30, S40, and S50 are experiments for emulating the sun by using the second light source; and the steps S60 and S70 are thermogravimetric test. In this process, the order of using the first light source for performing aging test, experiments for emulating the sun by using the second light source, and thermogravimetric test is not fixed. They can be changed according to experimental needs, not limited to the flow shown in FIG. 1B.

Figure 1C:
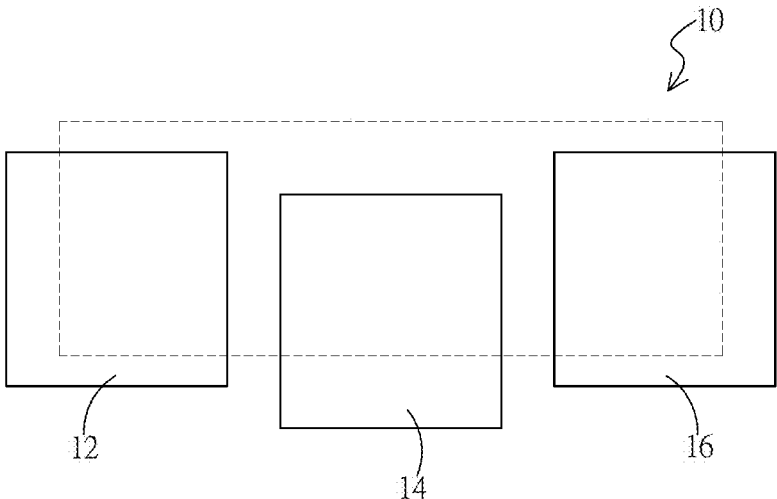
FIG. 1C shows a schematic diagram of the first detection part, the second detection part, and the third detection part on the same sample according to an embodiment of the present application.

According to the present embodiment, please refer to FIG. 1C, which shows a schematic diagram of the first detection part, the second detection part, and the third detection part on the same sample according to an embodiment of the present application. As shown in FIG. 1C, an object 10 includes a first detection part 12, a second detection part 14, and a third detection part 16. The first detection part 12, the second detection part 14, and the third detection part 16 can be given by dividing the object 10 into three parts for subsequent detection, as shown in FIG. 1C. By dividing the object 10 like dividing a cake, three detection parts are given for experiments.

According to the present embodiment, the object 10 is composed of recycled plastic materials and/or non-recycled plastic materials. Furthermore, the recycled plastic materials and the non-recycled plastic materials are selected from the group consisting of polyethylene, polypropylene, polyethylene terephthalate, polycarbonate, copolymer of polycarbonate and acrylonitrile butadiene styrene, polystyrene, or thermoplastic polyurethane.

Before the step S5, the method further comprises steps of:

Step S1: Obtaining a first yellowness index by detecting a standard object using the spectrophotometer;

Step S2: After illuminating the standard object using the first light source, obtaining a second yellowness index of the standard object using the spectrophotometer;

Step S3: Obtaining a standard yellowing index according to the second yellowness index and the first yellowness index.

Before the UV aging test, a standard object (not shown in the figure) is taken first. The standard object is identical to the object 10 and is an object containing no recycled plastic material.

In the steps S1 to S3, obtain a first yellowness index by detecting the standard object using the spectrophotometer. After illuminating the standard object using the first light source, obtain a second yellowness index of the standard object using the spectrophotometer. Finally, obtain a standard yellowing index according to the second yellowness index and the first yellowness index.

Next, after acquiring the standard yellowing index, please refer to FIG. 1A or 1B. The steps S5, S10, and S20 are the aging test using the first light source according to the present embodiment. Detect a fundamental yellowness index of the first detection part 12 using a spectrophotometer. Illuminate the first detection part 12 using a first light source for performing aging test.

The first light source according to the above embodiment includes a UV light source, a xenon arc light source, a carbon arc light source, or a mercury light source. If the first light source is a UV light source, the wavelength of the UV light source is from 200 nm to 400 nm.

According to the present embodiment, please refer to FIG. 1E, which shows a flowchart of the first light source according to an embodiment of the present application. As shown in the figure, after the step S10, the method further comprises a step of:

Step S11: The first light source illuminating the first detection part according to an illumination time.

According to the present embodiment, the first light source illuminates the first detection part 12 and obtaining a yellowing index according to the yellowness index and the fundamental yellowness index The above-mentioned spectrophotometer is a precision optical instrument that measures color differences through the principle of light and electrical conversion. It is a color identification instrument designed based on the principle of a spectrophotometer. The spectrophotometer can measure the color value and locate the position of the color of the object 10 in a color space. By comparing the object 10 with a standard color sample, the difference between the object 10 and the standard color sample is obtained. The spectrophotometer is widely used in metal, ceramics, plastics, coatings, textiles, printing, and chemical industries.

Next, please refer to FIG. 1A or 1B again. In the steps S30 to S50, before detection, extract a first surface image 141 of the second detection part 14 using an image extraction device (not shown in the figures). After capturing the first surface image 141, in a detection time, spray a water spray on the surface of the second detection part 14 and then illuminate the second detection part 14 using a second light source. The second light source includes a UV light source, a xenon arc light source, a carbon arc light source, or a mercury light source. If the second light source is a UV light source, the wavelength of the UV light source is from 200 nm to 400 nm.

Please refer to FIG. 1F, which shows a flowchart of the second light source according to an embodiment of the present application. As shown in the figure, the method further comprises steps of:

Step S41: In a first time interval, illuminating a surface of the second detection part using the second light source; and Step S42: In a second time interval, spraying the water spray to the second detection part.

In the step S41 of the present embodiment, in a first time interval, first illuminate a surface of the second detection part 14 using the second light source. The xenon arc light source will increase the temperature of the surface to a first temperature from 50° C. to 80° C.

Next, in the step S42, further in a second time interval, spray the water spray to the second detection part 14. The second light source is shut off while spaying the water spray. The first time interval and the second time interval are executed repeatedly and cyclically in the detection time. According to the present embodiment, after repeating the above two time intervals of the detection time, extract a second surface image 142 of the second detection part 14 using the image extraction device.

Figure 2A:
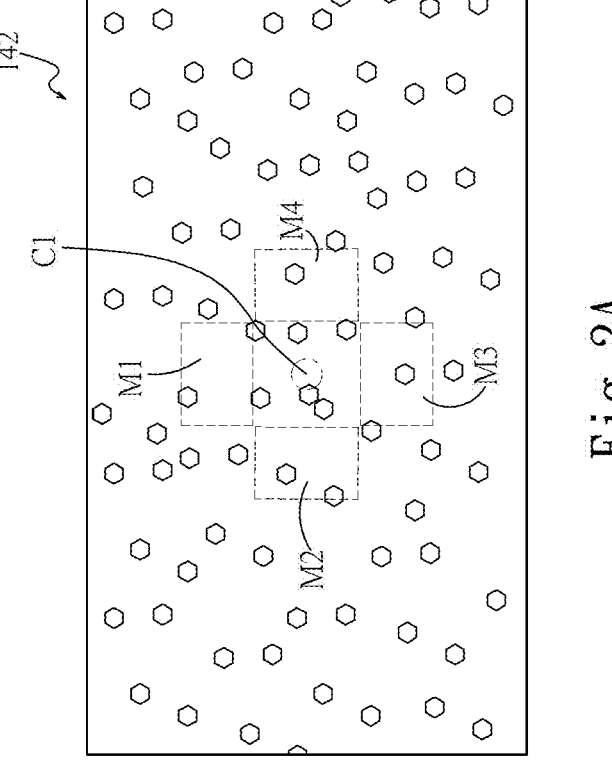
FIG. 2A shows a schematic diagram of image extraction according to an embodiment of the present application.

Please refer to FIG. 2A, which shows a schematic diagram of image extraction according to an embodiment of the present application. As shown in FIG. 2A, in the first surface image 141 and the second surface image 142, a central observation point C1 is first marked on the surface of the second detection part 14. Then the image extraction device focuses at the central observation point C1. By taking the central observation point C1 as the center, it takes a first image M1 above the center, a second image M2 below the center, a third image M3 to the left of the center, and a fourth image M4 to the right of the center.

The second light source described in the present embodiment is an artificial climate emulation test that emulates natural sunlight. It is usually adopted for accelerated light resistance and weather resistance tests of various materials or products. It is known that this method is used to screen new materials, improve existing materials, or evaluate the durability of materials after changes in composition.

Next, please refer to FIGS. 1A and 1B again. In the steps S60 and S70, place the third detection part 16 in a detection chamber of a thermogravimetric analyzer and enable a thermogravimetric variation of the third detection part 16 in the detection chamber; the thermogravimetric analyzer analyzes and calculates according to the thermogravimetric variation and obtains an activation energy value.

Please refer to FIG. 1G, which shows a flowchart of the standard activation energy value according to an embodiment of the present application. As shown in the figure, before the step S60, the method further comprises steps of:

Step S61: Placing a standard object in the detection chamber, and adjusting a chamber temperature of the detection chamber for enabling the standard object to produce a standard thermogravimetric variation in the detection chamber; and Step S62: The thermogravimetric analyzer analyzing and calculating according to the standard thermogravimetric variation and obtaining a standard activation energy value.

According to the present embodiment, place the standard object in the detection chamber, and adjust the chamber temperature of the detection chamber to enable a standard thermogravimetric variation of the standard object. The thermogravimetric analyzer analyzes and calculates according to the standard thermogravimetric variation and obtains a standard activation energy value. The chamber temperature is from 20° C. to 1000° C.

Next, perform thermogravimetric analysis on the third detection part 16. Please refer to FIG. 1H, which shows a flowchart according to an embodiment of the present application. As shown in the figure, the step S70 further includes the following steps:

Step S71: Adjusting a chamber temperature of the detection chamber; and

Step S72: The thermogravimetric analyzer obtaining the thermogravimetric variation of the third detection part according to a temperature variation of the chamber temperature.

According to the present embodiment, after placing the third detection part 16 in the detection chamber of the thermogravimetric analyzer, adjust the chamber temperature by gradual increasing in a temperature gradient or/and by repeated cyclic increasing and decreasing of temperatures for detecting the third detection part 16. After detection, the thermogravimetric variation of the third detection part 16 can be given.

According to the present embodiment, the thermogravimetric analyzer analyzes and calculates according to the thermogravimetric variation and gives the activation energy value of the third detection part 16.

According to the present embodiment, the thermogravimetric analyzer puts the sample under a certain temperature program control (rising/falling/constant temperature). Observe the changing process of sample mass with temperature or time. Obtain relevant information such as weight loss ratio, weight loss temperature, and decomposition residual amount. Based on the slope of each point on the weight loss curve, the weight loss rate at each temperature can be calculated, and thus the decomposition rate constant and reaction activation energy value of the third detection part 16 can be calculated.

According to the present embodiment, the Arrhenius equation, namely Equation 1, is adopted for calculation. k(T) is the variation of the rate constant.

$$k(T) = k_0 \ e^{-E_a/RT} \qquad \text{Equation 1}$$

Taking the logarithm of the reaction rate using the Arrhenius equation gives a curve in the XY format. By referring to the algorithm disclosed in ASTM (American Society for Testing and Materials International) for performing calculations on reaction rate, the activation energy value (Ea) of the object 10 and the standard activation energy value (Ea) of the standard object can be deduced.

Finally, as described in the step S80, compare the yellowing index with a standard yellowing index of a standard object, a first defect condition of the first surface image with a second defect condition of the second surface image, and the activation energy value with a standard activation energy value of a standard object. When the yellowing index is smaller than the standard yellowing index, the second defect condition is greater than the first defect condition, and the activation energy value is smaller than the standard activation energy value, the object is judged to contain recycled plastic materials.

illuminant D65; Standard view: CIE 1964 standard observer; Measurement aperture: $\psi25.4$ mm; Measurement increment: 10 nm; Wavelength range: 360 nm~740 nm; Measurement mode: Transmissive. The experiment results are shown in Table 1 below. Table 1 shows the comparative table between the yellowness index of the object and the standard yellowness index of the standard object.

TABLE 1

| Comparative table between the object and the standard object | | | | | |
|---|---|---|---|---|---|
| The object | | | The standard object | | |
| Yellowness chromaticity | Yellowness chromaticity (illuminated) | Difference in yellowness chromaticity | Yellowness chromaticity | Yellowness chromaticity (illuminated) | Difference in yellowness chromaticity |
| 0.34 | 1.00 | 0.66 | 0.17 | 1.05 | 0.89 |
| Yellowness index | Yellowness index (illuminated) | Difference in yellowness index | Yellowness index | Yellowness index (illuminated) | Difference in yellowness index |
| 0.33 | 1.56 | 1.23 | 0.26 | 1.89 | 1.63 |

In other words, when a user acquires the object 10 (single or multiple), the supplier of the object 10 will also provide the standard object containing no recycled plastic material. Before testing the object 10, the standard yellowing index and the standard activation energy value will be acquired first by testing.

Next, the user take the first detection part 12, the second detection part 14, and the third detection part 16 from the object 10 for performing the illumination experiment of the first light source, the illumination experiment of the second light source, and the experiment of thermogravimetric analyzer to obtain the yellowing condition, the surface image, and the activation energy value of the object 10. According to the three data along with the standard yellowing index and the standard activation energy value, whether the object 10 contains recycled plastic materials can be judged.

The advantage of the present embodiment is that the illumination experiment of the first light source, the illumination experiment of the second light source, and the experiment of thermogravimetric analyzer can be performed concurrently to obtain the yellowing condition, the surface image, and the activation energy value of the object 10. Thereby, whether the object 10 contains recycled plastic materials can be judged quickly.

Next, the object 10 being a PET is taken as an embodiment for illustration. First, a PET (the object 10) is divided into the first detection part 12, the second detection part 14, and the third detection part 16. The conditions of Experiment 1, Experiment 2, and Experiment 3 are described as follows.

1. Experiment 1: Adjust experimental parameters with reference to the test methods of ASTM to perform the experiment.
   Lamp: UV lamp (the first light source);
   Illumination energy: 0.3~1.5 $W/m^2$;
   Condition in one cycle: Continuous illumination, blackboard temperature 50° C.-80° C. (the first temperature); and
   Continuous illumination time: 24~450 hours.
   After illumination, a spectrophotometer (MINOLTA) is used for measurement with the condition: Light source: CIE The standard yellowness index of the standard object and the yellowness index of the object 10 include the difference in yellowness chromaticity and the difference in yellowness index. According to the present experiment, it can be seen from Table 1 that the difference in yellowness chromaticity and the difference in yellowness index in the yellowing index of the object 10 are smaller than the difference in yellowness chromaticity and the difference in yellowness index in the standard yellowing index (of the object containing no recycled plastic material). Thereby, by inspection using the UV light source, the standard yellowing index of the standard object and the yellowing index of the object 10 can be compared. When the yellowing index of the object 10 is smaller than the standard yellowing index, it is judged that the object 10 contains the recycled plastic material.

2. Experiment 2: Adjust experimental parameters with reference to the test methods of ISO (International Organization for Standardization) to conduct the illumination experiment using the second light source. The second light source in Experiment 2 is a xenon light source.
   Lamp: Xenon arc lamp (the second light source);
   Filter: Daylight;
   Illumination energy: 0.3~1.5 $W/m^2$;
   Condition in one cycle: Illumination for 85-150 minutes, standard blackboard temperature 50-80±3° C., ambient temperature 38±3° C., relative humidity 50±10% RH, illumination and humidification for 18 minutes; and
   Continuous illumination time: 24~450 hours.

Before the illumination experiment of the xenon arc light source, the first surface image 141 of the second detection part 14 is captured with the image extraction device (OLYMPUS Optical Microscope). After the illumination experiment of the xenon arc light source, the second surface image 142 is captured.

Please refer to FIG. 2A again for the method of capturing image using the image extraction device. The central observation point C1 is first marked on the surface. Then the image extraction device focuses at the central observation point C1. By taking the central observation point C1 as the center, it takes a first image M1 above the center, a second image M2 below the center, a third image M3 to the left of the center, and a fourth image M4 to the right of the center.

Take and compare the first image M1, the second image M2, the third image M3, and the fourth image M4 of the first surface image 141 and the first image M1, the second image M2, the third image M3, and the fourth image M4 of the second surface image 142, respectively.

The method to take the first image M1, the second image M2, the third image M3, and the fourth image M4 of the first surface image 141 of the standard object and the first image M1, the second image M2, the third image M3, and the fourth image M4 of the second surface image 142 of the standard object is the same as the method above. Hence, the details will not be described.

Figure 2B:
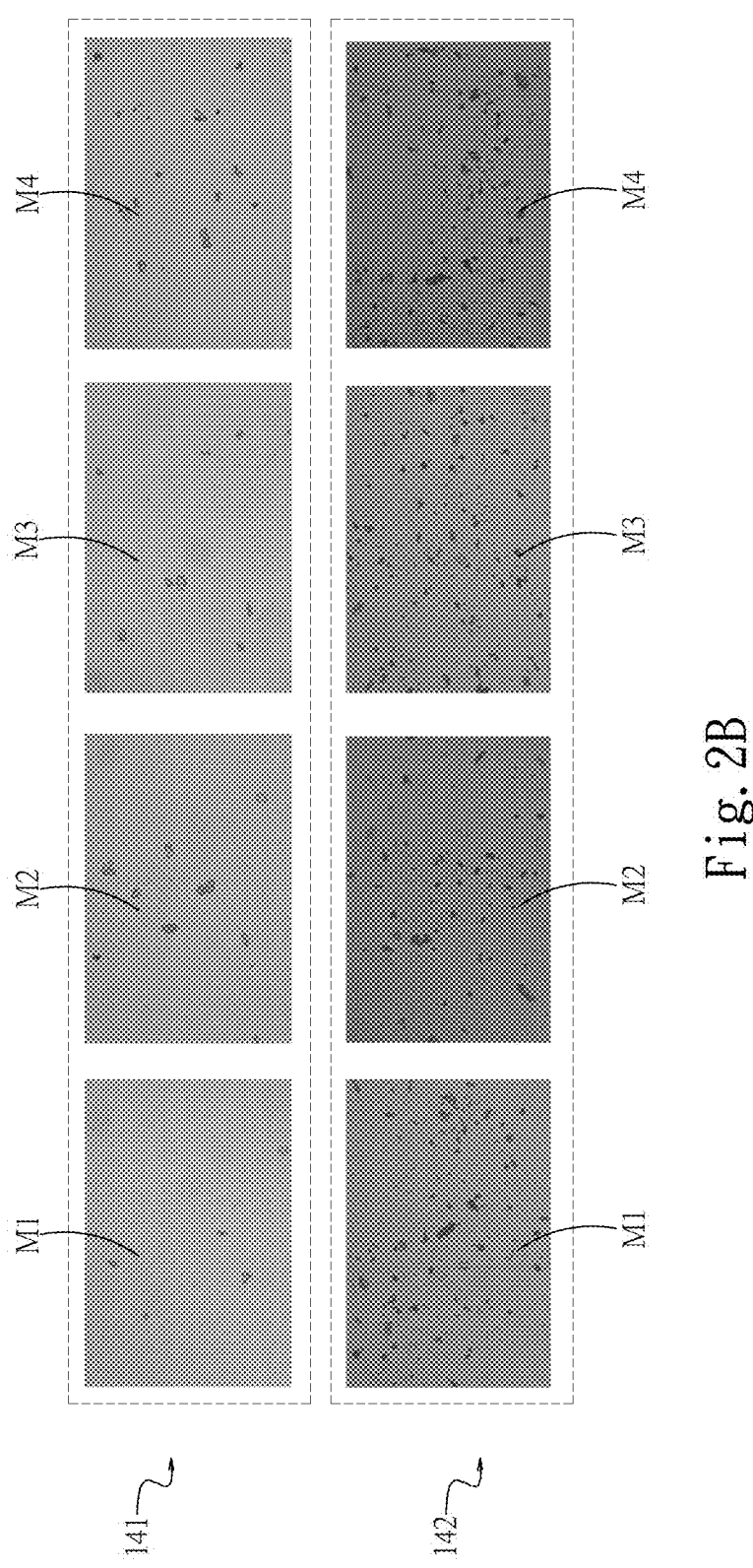
FIG. 2B shows a schematic diagram of the first image and the second image of containing recycled plastic materials according to an embodiment of the present application.

The comparison result is shown in FIG. 2B, which shows a schematic diagram of the first image and the second image of containing recycled plastic materials according to an embodiment of the present application. As shown in the figure, the image comparison result is shown clearly. After illuminating by the xenon arc light source on the second detection part 14, the defect amount of the second defect condition (the second surface image 142) is much greater than the defect amount of the first defect condition (the first surface image 141).

Figure 2C:
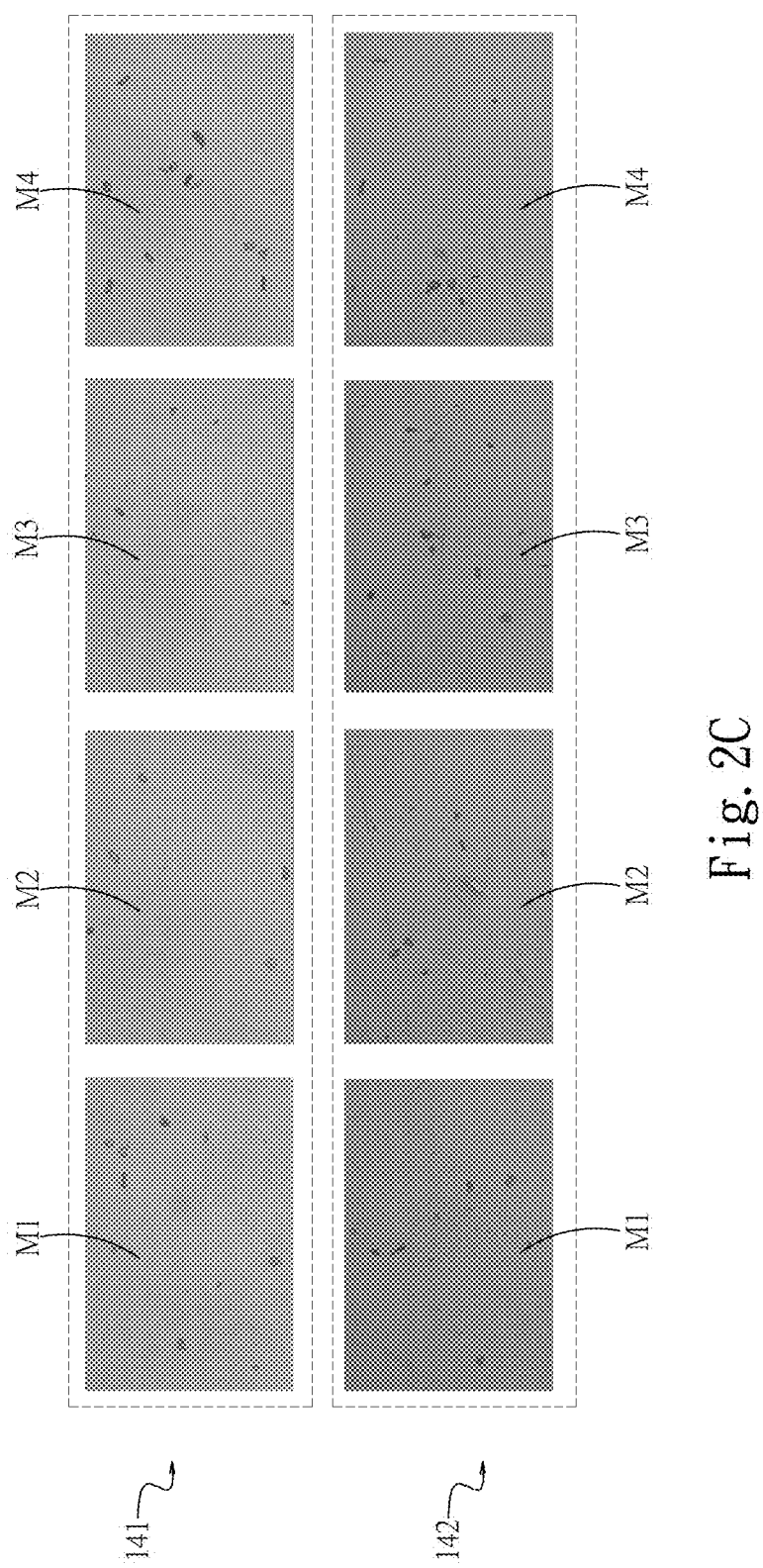
FIG. 2C shows a schematic diagram of the first image and the second image of containing no recycled plastic material according to an embodiment of the present application.

For the result of the first image 141 and the second image 142 of the standard object, please refer to FIG. 2C, which shows a schematic diagram of the first image and the second image of containing no recycled plastic material according to an embodiment of the present application. After illuminating by the xenon arc light source on the second detection part 14, the defect amount of the second defect condition is identical to the defect amount of the first defect condition. The illumination does not increase the defect amount of the surface defect condition on the standard object.

According to the comparison results of the second detection part 14 of the object 10 and the standard object, the standard object is an object containing no recycled plastic material. According to the experimental results, it can be confirmed that when the object 10 contains the recycled plastic materials, after illumination by the xenon arc light source, more defects will appear on the surface. Contrarily, when the object 10 contains no recycled plastic material, after illumination by the xenon arc light source, no excessive defects will appear. Accordingly, by comparing the defect amount, whether the object 10 contains the recycled plastic materials can be confirmed.

3. Experiment 3: Adjust experimental parameters with reference to the test methods of ASTM to conduct material kinetic activation energy value analysis. Perform thermogravimetric analysis experiments on the objects 10 containing 0%, 10%, 50%, and 100% of the recycled plastic material. The object 10 containing 0% of the recycled plastic material is the standard object. The objects 10 containing 10%, 50%, and 100% of the recycled plastic material are detection objects. The standard object gives the standard activation energy value. The activation energies for different proportions are given according to the objects 10 containing 10%, 50%, and 100% of the recycled plastic material.

Figure 3:
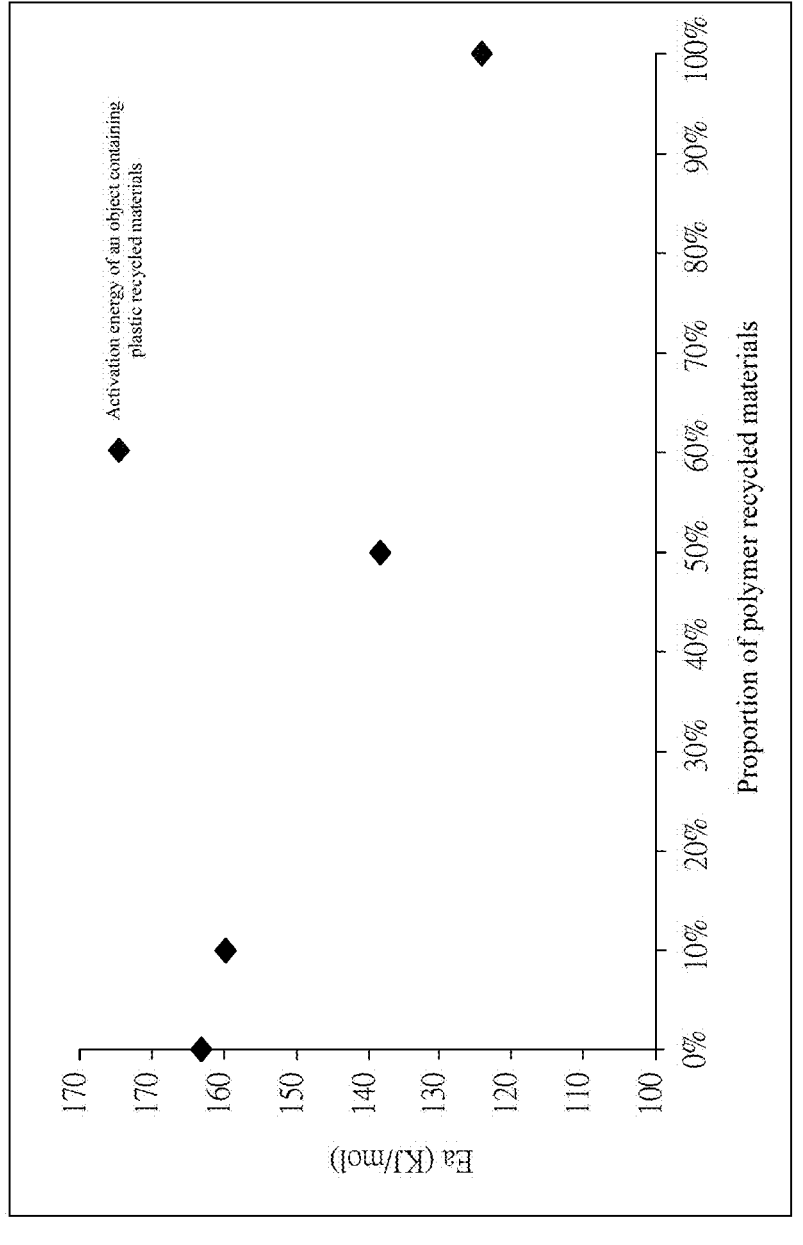
FIG. 3 shows a schematic diagram of the activation energy value according to an embodiment of the present application.

The experimental result is shown in FIG. 3, which shows a schematic diagram of the activation energy value according to an embodiment of the present application. As shown in FIG. 3, when the object 10 contains the recycled plastic material, the activation energy value is smaller than the standard object containing no recycled plastic material. Thereby, when the activation energy value of the object 10 is smaller than the standard activation energy value of the standard object, it can be confirmed that the object 10 contains the recycled plastic material.

Accordingly, it is known from Experiment 1, Experiment 2, and Experiment 3 that when the yellowing index of the object 10 is smaller than the standard yellowing index, the effect amount of the second defect condition is greater than the defect amount of the first defect condition, and the activation energy value is smaller than the standard activation energy value, it is judged that the materials for manufacturing the plastic material of the object 10 contains recycled plastic materials.

The above examples illustrate the embodiments of the present application. The present application provides a method for detecting an object containing recycled plastic materials. The method observes the yellowing condition of an object using a first light source. By illuminating the object using a second light source, an image extraction device observes the defect condition through the image of object surface. Then a thermogravimetric analyzer is used to analyze and calculate the activation energy value of the object according to the thermogravimetric variation of the object. By comparing the yellowing condition, the surface effect image, and the activation energy value of the object with the standard yellowing index, the defect condition, and the standard activation energy value of the standard object, whether the object contains recycled plastic materials can be judged. According to the method of the present application, whether an object contains recycled plastic materials can be judged quickly.

Furthermore, please refer to FIG. 4, which shows a flowchart according to another embodiment of the present application. As shown in FIG. 4, the method for detecting an object containing recycled plastic materials by qualitative and semi-quantitative detections. The method comprise steps of:

Step S91: Adding a detection object into a glass beaker;

Step S92: Adding a sodium hydroxide solution into the glass beaker, covering the glass beaker with a watch glass lid, and performing an extraction process for forming an extraction sample;

Step S93: Rinsing the extraction sample on the glass beaker and the watch glass lid using a deionized water to form an extraction liquid;

Step S94: Adding a 4,4,-bis(2-benzoxazolyl) stilbene to the extraction liquid and a PET sample solution, respectively, and performing a fluorescence spectrum analysis in an analysis condition to obtain a detection spectrum and a native PET spectrum;

Step S95: Analyzing and comparing the detection spectrum and the native PET spectrum; and Step S96: When the detection spectrum is not equal to the native PET spectrum, judging that the detection object contains a recycled PET.

As shown in the step S91, place a detection object (around 2.5 g) into a 200 mL glass beaker. Before placing into the glass beaker, the detection object is preprocessed by first cutting into 15 cm×15 cm pieces and then into 1 cm×1 cm pieces.

In the step S92, add a 30 mL 10% sodium hydroxide solution into the glass beaker (along with a magnet). Cover the glass beaker with a watch glass lid and place them on a hot plate with temperature control for performing an extraction process at the temperature from 105 to 125° C. for 70 to 100 minutes (preferably 90 minutes) for forming an extraction sample. When the extraction sample is finished, remove the glass beaker from the hot plate and cool for approximately 20 minutes.

Next, as shown in the step S93, rinse the extraction sample on the glass beaker and the watch glass lid using a 40 mL deionized water divided to multiple times with small amount each time to form an extraction liquid.

Then, as shown in the step S94, place 10 mL of the extraction liquid, 10 mL of a PET sample solution (acquired by the steps S91 to S93 using 100% native PET plastic materials), 10 mL of a blank solution (containing deionized water only), 10 mL of 10% the sodium hydroxide solution, and 10 mL of 100% recycled PET solution (acquired by the steps S91 to S93 using 100% recycled PET (rPET)) into 25 mL clean glass test tubes with cap, respectively. In addition, these solutions are placed into plastic test tubes in small amount, respectively.

Before performing a fluorescence spectrum analysis, observed the respective solutions in the plastic test tubes. It is observed that the extraction liquid is slightly turbid and has poor transmittance. On the contrary, the PET sample solution is relatively clear with better transmittance.

Next, add a 4,4,-bis(2-benzoxazolyl) stilbene (BBS, which is a fluorescent dye approved by the US FDA for use in food/non-food contact products) to the solutions in the 25 mL clean glass test tubes with cap, respectively, and perform fluorescence spectrum analysis in an analysis condition. The analysis condition includes that the excitation wavelength is set at 373 nm; the incident slit is set at 5 nm; the emission slit is set at 5 nm; the wavelength scanning range is set from 360 nm to 800 nm; and the scanning rate is set within 120 nm/min. As a result, a detection spectrum (for the extraction liquid), a native PET spectrum (for the PET sample solution), a blank solution spectrum (for the blank solution), an alkaline solvent spectrum (for the sodium hydroxide solution), and an rPET spectrum (for the 100% recycled PET materials solution) are given.

While performing fluorescence spectrum analysis, record the corresponding fluorescence spectrum of respective solutions (the extraction liquid, the PET sample solution, the blank solution, 10% the sodium hydroxide solution, and the 100% recycled PET materials solution). In addition, while exciting using the wavelength 373 nm, the fluorescence intensity at the wavelength 445 nm is recorded (for calculating the added 0.05% BBS concentration (QE quantitative value)); the fluorescence intensity around at the wavelength 746 nm is also observed.

In the measurement of the step S94, the fluorescence intensity at the wavelength 445 nm should be recorded. If the peak of the emission spectrum deviates from 445 nm, the excitation wavelength should be adjusted until it falls at 445 nm before reading the fluorescence intensity. Record the adjusted excitation wavelength.

According to research, the threshold aggregation concentration in fluorescent and nonfluorescent dye-polymer systems depends on the crystallinity of polymer host, the relative solubility of dye (guest), and the number of dye-polymer (guest-host) interactions.

BBS dyes belong to this class of conjugated π system fluorophores with aggregation-induced enhanced emission (AIEE). When the fluorophores are dispersed in a continuous matrix, the fluorescent dye concentration increases, and the formation energy and the dissociated recycled plastic molecular groups aggregate, aggregation and color development will occur.

Therefore, after utilizing the aggregation-induced interaction between the BBS dyes and the recycled PET molecules that are ionized and dissociated in the solution and after excitation, the negative Coulomb coupling between the aggregated molecules reduces the first excited state energy and the red shift enhances the fluorescence emission. The resulting aggregates can exhibit different photophysical properties relative to their monomeric counterparts.

At present, most of the manufacturing processes of recycled plastics use a physical mixing chain method to produce native plastics and recycled PET (recycled polymer) in a melting and granulating reprocessing process. Regenerated plastics formed from a plastic matrix of a single component or composite components have weak intermolecular bonds and changes in molecular crystallinity.

Accordingly, when an alkaline solution is used as a solvent for sample extraction and heated to form a single component or composite components of recycled plastics, the bonds between the molecules weaken and the crystallinity of the molecules changes. Consequently, the molecules of recycled PET are easy to dissociate and ionize and can exist stably in the solution.

Figure 5A:
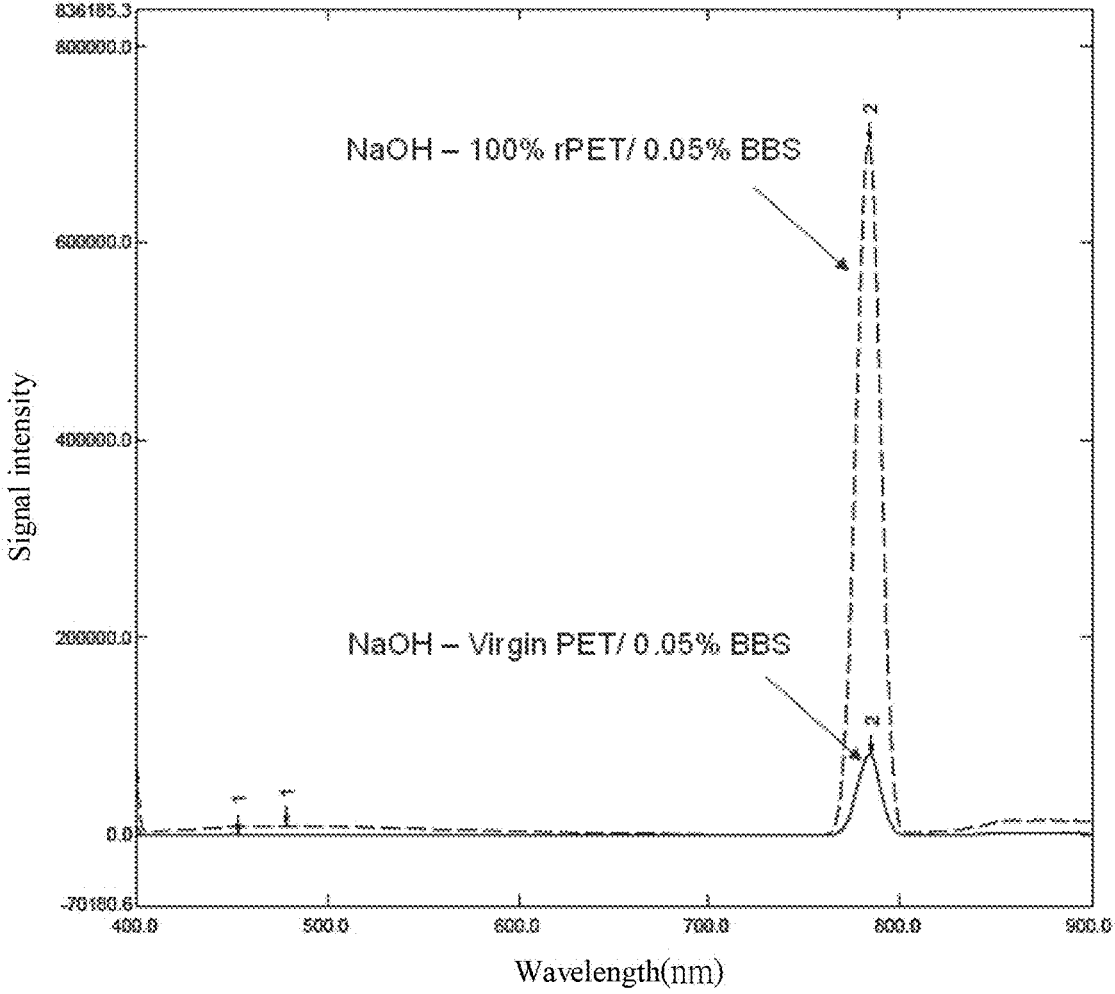
FIGS. 5A-5C show comparative spectral overlay diagrams according to another embodiment of the present application.
Figure 5B:
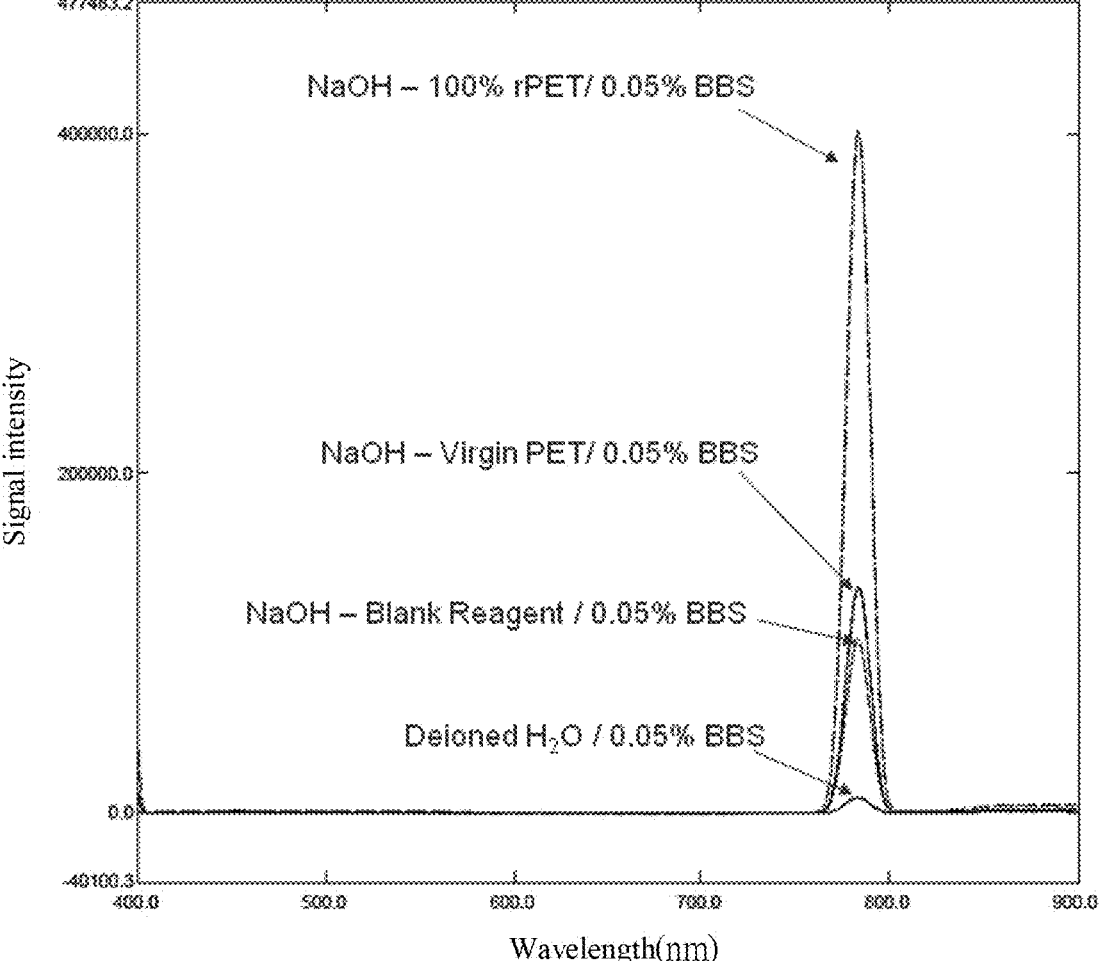
Figure 5C:
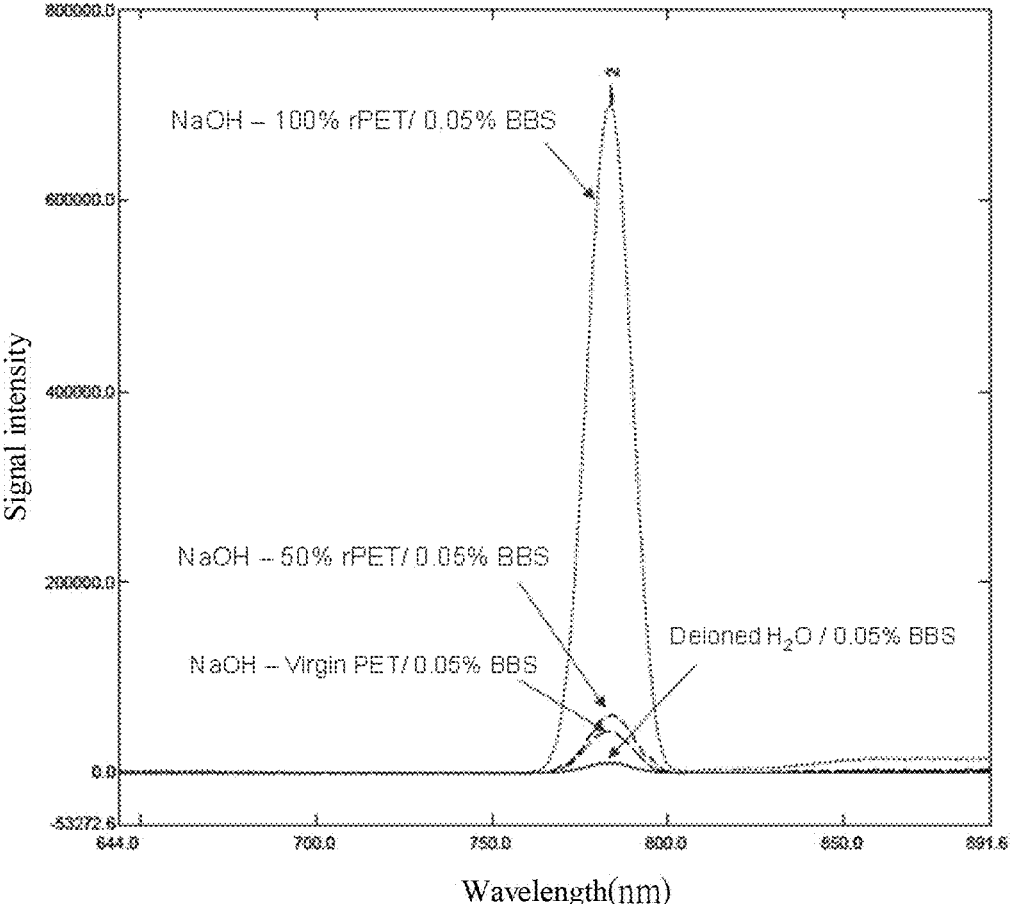

Thereby, when the detection object contains a higher proportion of recycled PET, more molecular groups of the recycled PET will dissociate and ionize after extraction. Contrarily, 100% native PET plastics have strong intermolecular crystallinity and strong intermolecular bonding. After extraction, it is less likely to cause the plastic molecular groups to dissociate and ionize. Therefore, the spectrum formed will also be different. FIGS. 5A-5C show comparative spectral overlay diagrams according to another embodiment of the present application.

As shown in FIG. 5A, 10 mL of the PET sample solution and 10 mL of the 100% recycled PET solution are added by 2 mL of the fluorescent dye 4,4,-bis(2-benzoxazolyl) stilbene (BBS). After reaction for 15 minutes, perform excitation with the wavelength 373 nm and observe the spectrum overlay diagram of the emission double-frequency wave at 746 nm. It can be observed form FIG. 5A that since the molecules of the recycled PET in the 100% recycled PET solution (NaOH-100% rPET/0.05% BBS) are easy to dissociate, its signal intensity will be greater than that of the PET sample solution (NaOH-Native PET/0.05% BBS).

Next, as shown in FIG. 5B, 10 mL of 10% the sodium hydroxide solution, 10 mL of the PET sample solution, 10 mL of the blank solution (containing deionized water only), and 10 mL of the 100% recycled PET solution are added by 2 mL of the fluorescent dye 4,4,-bis(2-benzoxazolyl) stilbene (BBS). After reaction for 15 minutes, perform excitation with the wavelength 373 nm and observe the spectrum overlay diagram of the emission double-frequency wave at 746 nm. It can be observed form FIG. 5B that since the molecules of the recycled PET in the 100% recycled PET solution (NaOH-100% rPET/0.05% BBS) are easy to dissociate, its signal intensity will be greater than that of the PET sample solution (NaOH-Native PET/0.05% BBS), as well as being apparently different from the signal intensity of the 10% sodium hydroxide solution (NaOH-Blank reagent/0.05% BBS) and 10 mL of the blank solution (deionized water/0.05% BBS).

After the fluorescence spectrum analysis, the steps S95 and S96 are executed for analyzing and comparing the detection spectrum and the native PET spectrum (with reference to the spectrum diagrams of blank solution, alkaline solvent, and rPET). When the detection spectrum is not equal to the native PET spectrum, judge that the detection object contains a recycled PET.

Alternatively, in addition to the fluorescent spectrum analysis, the color judgement analysis can be performed. After the step S93, the method further comprises steps of:

Step S931: Filtering the extraction liquid and the PET sample solution to form a detection sample and a native PET sample;

Step S932: Baking the detection sample and the native PET sample, and recording a detection color of the detection sample and a PET color of the native PET sample; and Step S933: Comparing the detection color with the PET color, and judging that the detection object contains a recycled PET when the detection color is different from the PET color.

As shown in the step S931, place the extraction liquid and the PET sample solution in 5 mL clean glass test tubes with cap, respectively, and perform filtering using a glass funnel with 0.45 μm filter (disposing a cleaned and dried 0.45 μm filter in a glass conical flask) to form a detection sample and a native PET sample. Weigh the samples, respectively.

Next, as shown in the step S932, bake the detection sample and the native PET sample in a clean crucible, respectively, at a temperature from 90 to 120° C. (preferably 110° C.) for 6 to 9 hours (preferably 8 hours). After cooling, record a detection color of the detection sample and a PET color of the native PET sample, respectively. In addition, weigh the samples again, respectively.

Finally, as shown in the step S933, compare the detection color (ranging from light yellow to khaki gray if containing the recycled PET) with the PET color (ranging from matte white to light gray). Judge that the detection object contains a recycled PET when the detection color is different from the PET color.

The present application is based on the basic law of light absorption, the Beer-Lambert law. When light passes through a solution, it will be influenced by the high or low concentration of solute in the solution, which will influence the transmitted light. Therefore, when the solute concentration in the solution is high, the transmitted light is low. On the contrary, when the solute concentration in the solution is low, the transmitted light is high, just as described by the Beer-Lambert law.

As shown in the step S933, when an alkaline solution is used as a solvent for sample extraction, since the molecules of recycled PET are easier to dissociate and ionize than the molecules of 100% native PET, the former can exist stably in the solution. For 100% native PET, Because of its strong intermolecular crystallinity and intermolecular bonding, after extraction, it is less likely to cause the plastic molecular groups to dissociate and ionize.

Contrarily, the bonds between the molecular groups of the recycled PET are relatively fragile. When an alkaline solution is used as a solvent for sample extraction, more of its molecular groups will dissociate and ionize. The changes in color depth after extraction of the tested samples can be compared. Therefore, it can be used to deduce the recycling amount of the recycled PET added to the plastic material. The Beer-Lambert law is a general law that applies to uniform and non-scattering solutions.

The present application provides a method for detecting an object containing recycled plastic materials by qualitative and semi-quantitative detections. Please refer to FIG. 4. As shown in FIG. 4, after the step S95, the method further comprises a step S951: analyzing to obtain the proportion of a recycled PET in the detection object according to the difference ratio between the detection spectrum and the native PET spectrum.

When an alkaline solution is used as a solvent for sample extraction, the molecules of recycled PET are easy to dissociate and ionize and can exist stably in the solution.

Thereby, more molecular groups of the recycled PET will dissociate and ionize after extraction. Contrarily, 100% native PET plastics have strong intermolecular crystallinity and strong intermolecular bonding. After extraction, it is less likely to cause the plastic molecular groups to dissociate and ionize. Therefore, the spectrum formed will also be different. Different content of the recycled PET also leads to different spectrum.

Please refer to FIG. 5C. As shown in FIG. 5C, 10 mL of the 10% sodium hydroxide solution, 10 mL of the PET sample solution, 10 mL of the 50% recycled PET solution, and 10 mL of the 100% recycled PET solution are added by 2 mL of the fluorescent dye 4,4,-bis(2-benzoxazolyl) stilbene (BBS). After reaction for 15 minutes, perform excitation with the wavelength 373 nm and observe the spectrum overlay diagram of the emission double-frequency wave at 746 nm. It can be observed form FIG. 5C that since the molecules of the recycled PET in the 100% recycled PET solution (NaOH-100% rPET/0.05% BBS) are easy to dissociate, its signal intensity will be greater than that of the PET sample solution. Besides, the molecules of the recycled PET in the 50% recycled PET solution (NaOH-50% rPET/0.05% BBS) will dissociate as well. Nonetheless, the amount of dissociation is less than that of the 100% recycled PET solution. Thereby, the signal intensity of the 50% recycled PET solution will be between the signal intensity of the 100% recycled PET solution (NaOH-100% rPET/0.05% BBS) and the signal intensity of the PET sample solution (NaOH-Native PET/0.05% BBS), and be greater than the signal intensity of the 10% sodium hydroxide solution (NaOH-Blank reagent/0.05% BBS).

According to FIG. 5C, the present application can analyze to obtain the proportion of the recycled PET in the detection object according to the difference ratio between the detection spectrum and the native PET spectrum.

Accordingly, the present application makes use of the difference in bonding strength between molecules and adds appropriate fluorescent dyes dispersed in a continuous matrix. When the concentration of the fluorescent dye increases and the formation energy and the dissociated recycled plastic molecular groups aggregate, the excitation wavelength is set at 373 nm and observe the fluorescent intensity of the emission double-frequency wave at 746 nm. According to the above embodiment, it can be seen that at the double frequency of the excitation light source, the intensity of the scattered waves from the native and recycled plastic materials differ significantly. The property can be used to detect whether an object contains recycled plastic materials qualitatively. Moreover, the difference ratio in intensity can be used for quick semi-quantitative determination.

What is claimed is:

1. A method for detecting an object containing recycled plastic materials by qualitative and semi-quantitative detections, applied for obtaining and detecting an object, the object having a first detection part, a second detection part, and a third detection part, the method comprising steps of:

detecting a fundamental yellowness index of the first detection part using a spectrophotometer;

illuminating the first detection part using a first light source;

detecting a yellowness index of the first detection part using the spectrophotometer and obtaining a yellowing index according to the yellowness index and the fundamental yellowness index;

capturing a first surface image of the second detection part using an image extraction device;

illuminating the second detection part using a second light source the second detection part after spraying a water spray on the second detection part, in a detection time of detecting;

capturing a second surface image of the second detection part using the image extraction device;

placing the third detection part in a detection chamber of a thermogravimetric analyzer and enabling a thermogravimetric variation of the third detection part in the detection chamber;

analyzing and calculating according to the thermogravimetric variation and obtaining an activation energy value using the thermogravimetric analyzer;

comparing the yellowing index with a standard yellowing index of a standard object, a first defect condition of the first surface image with a second defect condition of the second surface image, and the activation energy value with a standard activation energy value of a standard object; and wherein when the yellowing index is smaller than the standard yellowing index, the second defect condition is greater than the first defect condition, and the activation energy value is smaller than the standard activation energy value, the object containing recycled plastic materials is determined.

2. The method for detecting an object containing recycled plastic materials by qualitative and semi-quantitative detections of claim 1, wherein the step of illuminating the first detection part using a first light source, the first light source includes a UV light source, a xenon arc light source, a carbon arc light source, or a mercury light source.

3. The method for detecting an object containing recycled plastic materials by qualitative and semi-quantitative detections of claim 2, wherein the wavelength of the UV light source is from 200 nm to 400 nm.

4. The method for detecting an object containing recycled plastic materials by qualitative and semi-quantitative detections of claim 3, wherein before the step of detecting the fundamental yellowness index of the first detection part using the spectrophotometer, further comprising steps of:

obtaining a first yellowness index by detecting a standard object using the spectrophotometer;

obtaining a second yellowness index of the standard object using the spectrophotometer after illuminating the standard object using the first light source;

obtaining a standard yellowing index according to the second yellowness index and the first yellowness index;

wherein the standard object is an object containing no recycled plastic material.

5. The method for detecting an object containing recycled plastic materials by qualitative and semi-quantitative detections of claim 4, wherein the step of illuminating the first detection part using a first light source, further comprising a step of:

illuminating the first detection part for an illumination time using the first light source;

wherein the illumination time is from 24 to 450 hours.

6. The method for detecting an object containing recycled plastic materials by qualitative and semi-quantitative detections of claim 1, wherein the step of illuminating the second detection part using the second light source the second detection part after spraying a water spray on the second detection part, in the detection time of detecting, the second light source includes a UV light source, a xenon arc light source, a carbon arc light source, or a mercury light source.

7. The method for detecting an object containing recycled plastic materials by qualitative and semi-quantitative detections of claim 6, wherein the step of illuminating the second detection part using the second light source the second detection part after spraying a water spray on the second detection part, in the detection time of detecting, further comprising steps of:

illuminating a surface of the second detection part in a first time interval using the second light source, wherein the surface is illuminated at a first temperature from 50° C. to 80° C.; and spraying the water spray to the second detection part in a second time interval, wherein the second light source is shut off while spaying the water spray;

wherein the first time interval and the second time interval are repeated cyclically in the detection time.

8. The method for detecting an object containing recycled plastic materials by qualitative and semi-quantitative detections of claim 7, wherein the step of illuminating the surface of the second detection part in the first time interval using the second light source, the first time interval is from 85 to 150 minutes.

9. The method for detecting an object containing recycled plastic materials by qualitative and semi-quantitative detections of claim 7, wherein the step of spraying the water spray to the second detection part in a second time interval, the second time interval is from 5 to 60 minutes.

10. The method for detecting an object containing recycled plastic materials by qualitative and semi-quantitative detections of claim 1, wherein before the step of placing the third detection part in a detection chamber of a thermogravimetric analyzer and enabling a thermogravimetric variation of the third detection part in the detection chamber, further comprising steps of:

placing a standard object in the detection chamber and adjusting a chamber temperature of the detection chamber for enabling the standard object to produce a standard thermogravimetric variation in the detection chamber; and analyzing and calculating the standard thermogravimetric variation to obtain a standard activation energy value using the thermogravimetric analyzer;

wherein the chamber temperature is from 20° C. to 1000° C.

11. The method for detecting an object containing recycled plastic materials by qualitative and semi-quantitative detections of claim 1, wherein the step of analyzing and calculating the standard thermogravimetric variation to obtain the standard activation energy value using the thermogravimetric analyzer, further comprising steps of:

adjusting a chamber temperature of the detection chamber, where the chamber temperature is from 20° C. to 1000° C.; and obtaining the thermogravimetric variation of the third detection part according to a temperature variation of the chamber temperature using the thermogravimetric analyzer.

12. The method for detecting an object containing recycled plastic materials by qualitative and semi-quantitative detections of claim 1, wherein the object is composed of recycled plastic materials and/or non-recycled plastic materials, the recycled plastic materials and the non-recycled plastic materials selected from the group consisting of polyethylene, polypropylene, polyethylene terephthalate, polycarbonate, copolymer of polycarbonate and acrylonitrile butadiene styrene, polystyrene, or thermoplastic polyurethane.

13. A method for detecting an object containing recycled plastic materials by qualitative and semi-quantitative detections, comprising steps of:

adding a detection object into a glass beaker;

adding a sodium hydroxide solution into the glass beaker, covering the glass beaker with a watch glass lid, and performing an extraction process for forming an extraction sample;

rinsing the extraction sample on the glass beaker and the watch glass lid using a deionized water to form an extraction liquid;

adding a 4,4,-bis(2-benzoxazolyl) stilbene to the extraction liquid and a PET sample solution, respectively, and performing a fluorescence spectrum analysis in an analysis condition to obtain a detection spectrum and a native PET spectrum;

analyzing and comparing the detection spectrum and the native PET spectrum; and when the detection spectrum is not equal to the native PET spectrum, the detection object contains a recycled PET.

14. The method for detecting an object containing recycled plastic materials by qualitative and semi-quantitative detections of claim 13, wherein before the step of adding the detection object into the glass beaker, the detection object undergoes a pre-processing procedure in advance, the pre-processing procedure is to cut the detection object into 1 cm×1 cm pieces.

15. The method for detecting an object containing recycled plastic materials by qualitative and semi-quantitative detections of claim 14, wherein the step of adding the sodium hydroxide solution into the glass beaker, covering the beaker with a watch glass lid, and performing an extraction process, the extraction temperature is from 105° C. to 125° C. and the extraction time is from 70 to 100 minutes.

16. The method for detecting an object containing recycled plastic materials by qualitative and semi-quantitative detections of claim 15, wherein the step of adding 4,4,-bis(2-benzoxazolyl) stilbene to the extraction liquid and the PET sample solution, respectively, and performing fluorescence spectrum analysis in an analysis condition, the analysis condition includes that the excitation wavelength is set at 373 nm; the incident slit is set at 5 nm; the emission slit is set at 5 nm; the wavelength scanning range is set from 360 nm to 800 nm; and the scanning rate is set within 120 nm/min.

17. The method for detecting an object containing recycled plastic materials by qualitative and semi-quantitative detections of claim 16, wherein after the step of rinsing the extraction sample on the glass beaker and the watch glass lid using the deionized water to form an extraction liquid, further comprising steps of:

filtering the extraction liquid and the PET sample solution to form a detection sample and a native PET sample;

baking the detection sample and the native PET sample, and recording a detection color of the detection sample and a PET color of the native PET sample; and comparing the detection color with the PET color, and judging that the detection object contains a recycled PET when the detection color is different from the PET color.

18. The method for detecting an object containing recycled plastic materials by qualitative and semi-quantitative detections of claim 17, wherein the step of baking the detection sample and the native PET sample, the baking temperature is from 90° C. to 120° C. and the baking time is from 6 to 9 hours.

19. A method for detecting an object containing recycled plastic materials by qualitative and semi-quantitative detections, the method comprising steps of:

adding a detection object into a glass beaker;

adding a sodium hydroxide solution into the glass beaker, covering the beaker with a watch glass lid, and performing an extraction process for forming an extraction sample;

rinsing the extraction sample on the glass beaker and the watch glass lid using a deionized water to form an extraction liquid;

adding 4,4,-bis(2-benzoxazolyl) stilbene to the extraction liquid and a PET sample solution, respectively, and performing a fluorescence spectrum analysis in an analysis condition to obtain a detection spectrum and a native PET spectrum;

analyzing and comparing the detection spectrum and the native PET spectrum; and analyzing and obtaining the proportion of a recycled PET in the detection object according to the difference ratio between the detection spectrum and the native PET spectrum.

20. The method for detecting an object containing recycled plastic materials by qualitative and semi-quantitative detections of claim 19, wherein before the step of adding the detection object into the glass beaker, the detection object undergoes a pre-processing procedure in advance, the pre-processing procedure is to cut the detection object into 1 cm×1 cm pieces.

21. The method for detecting an object containing recycled plastic materials by qualitative and semi-quantitative detections of claim 20, wherein the step of adding a sodium hydroxide solution into the glass beaker, covering the beaker with a watch glass lid, and performing an extraction process, the extraction temperature is from 105° C. to 125° C. and the extraction time is from 70 to 100 minutes.

22. The method for detecting an object containing recycled plastic materials by qualitative and semi-quantitative detections of claim 21, wherein the step of adding 4,4,-bis(2-benzoxazolyl) stilbene to the extraction liquid and the PET sample solution, respectively, and performing fluorescence spectrum analysis in an analysis condition, the analysis condition includes that the excitation wavelength is set at 373 nm; the incident slit is set at 5 nm; the emission slit is set at 5 nm; the wavelength scanning range is set from 360 nm to 800 nm; and the scanning rate is set within 120 nm/min.

* * * * *